(12) United States Patent
Barnicki et al.

(10) Patent No.: US 6,444,096 B1
(45) Date of Patent: Sep. 3, 2002

(54) PROCESS FOR THE RECOVERY AND PURIFICATION OF CYCLOBUTANONE

(75) Inventors: Scott Donald Barnicki; Timothy Richard Nolen, both of Kingsport; Robert Sterling Kline, Talbott; Dewey Wayne Fuller, Jr., Bristol; Mary Kathleen Foster, Jonesborough; Stephen Neal Falling, Kingsport, all of TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/639,540

(22) Filed: Aug. 16, 2000

(51) Int. Cl.$^7$ .............................. B01D 3/34; B01D 3/36; C07C 45/82; C07C 45/84
(52) U.S. Cl. ............................ 203/43; 203/49; 203/63; 203/64; 203/59; 203/60; 203/62; 203/67; 203/68; 203/69; 203/70; 203/75; 203/77; 203/80; 203/78; 568/366
(58) Field of Search ................................ 203/73, 74–80, 203/14, 17, 28, 43, 49, 63, 64, 68, 70, 60, 69, 62, 67, 59; 568/303, 364, 366

(56) References Cited

U.S. PATENT DOCUMENTS

| 2,647,861 A | 8/1953 | Drout, Jr. |
| 2,684,934 A | 7/1954 | Weaver, Jr. et al. |
| 4,186,059 A | 1/1980 | Fleck |
| 5,420,350 A * | 5/1995 | Nakayama .................. 568/364 |
| 6,248,927 B1 | 6/2001 | Floyd et al. |

FOREIGN PATENT DOCUMENTS

| EP | 0112261 | 6/1984 |
| FR | 7828329 | 4/1980 |
| GB | 640581 | 7/1950 |
| SU | 1567603 | 5/1990 |

OTHER PUBLICATIONS

Lee–Ruff, Advances in Strain in Organic Chemistry, (1991), vol. 1, pp. 167–213.
Bellus et al, Angew Chem. Int. Ed. Engl. 27, (1988), 100(6), pp. 797–827.
Krumpolc et al, Organic Synthesis Collective Volumes, pp. 114–116.

* cited by examiner

Primary Examiner—Virginia Manoharan
(74) Attorney, Agent, or Firm—Michael J. Blake

(57) ABSTRACT

A process for the recovery and purification of cyclobutanone from a crude product mixture obtained from an oxidation product mixture resulting from the oxidation of cyclobutanol to cyclobutanone in the presence of water. The process provides for the recovery of cyclobutanone in a purity of at least 90 weight percent by a combination of distillation steps.

13 Claims, No Drawings

PROCESS FOR THE RECOVERY AND PURIFICATION OF CYCLOBUTANONE

FIELD OF THE INVENTION

This invention pertains to a process for the recovery and purification of cyclobutanone from a crude product mixture obtained from an oxidation product mixture resulting from the oxidation of cyclobutanol to cyclobutanone. More specifically, this invention pertains to the recovery of cyclobutanone in a purity of at least 90 weight percent by a novel combination of distillation steps.

BACKGROUND OF THE INVENTION

Cyclobutanone is a valuable organic intermediate useful in the preparation of a variety of compounds. See, for example, Lee-Ruff, Adv. Strain Org. Chem, (1991), 1, 167 and Bellus et al., Angew Chem., (1988), 100(6), 820. Cyclobutanone can be prepared by the oxidation of cyclobutanol with chromium trioxide and oxalic acid in water as described, for example, by Krumpolic and Rocek in *Organic Synthesis Collective Volumes,* pages 114–116. The chromium trioxide/oxalic acid oxidation is relatively non-selective and produces a dilute aqueous crude cyclobutanone mixture containing many hard-to-separate impurities. Typical impurities in the crude aqueous cyclobutanone include, but are not limited to, cyclopropanemethanol, unreacted cyclobutanol, 3-butene-1-ol, 2-butene-1-ol, cyclopropane carboxaldehyde, cyclopropane carboxylic acid, ethers and mixed ethers of cyclobutanol, cyclopropanemethanol, 3-butene-1-ol, and 2-butene-1-ol; hemi-ketals and ketals of the cyclopropanemethanol, cyclobutanol, 3-butene-1-ol and 2-butene-1-ol with cyclobutanone as well as other unknown compounds with boiling points higher and lower than cyclobutanone. Many of these impurities are color bodies and which cause the cyclobutanone product to be highly colored if not removed.

Krumpolic and Rocek, supra, describe the extraction of the crude cyclobutanone-water mixture with methylene chloride and the drying of the organic phase, comprising cyclobutanone and other organic impurities, over anhydrous magnesium sulfate containing anhydrous potassium carbonate. The dried organic layer is distilled twice to remove methylene chloride and recover the cyclobutanone product. The procedure is said to produce a relatively pure cyclobutanone product, i.e., 98–99 weight percent cyclobutanone. However, this process suffers many disadvantages from a standpoint of practical large-scale production of high-purity cyclobutanone. The extracting agent, methylene chloride, is quite toxic, very volatile, and is costly to handle and dispose of safely. The aforementioned procedure specifies the use of approximately 86 kg of methylene chloride per kg of cyclobutanone produced. Thus, extraction and subsequent distillation equipment required must be very large and expensive relative to the amount of cyclobutanone produced. The authors disclose that cyclobutanone is highly soluble in water and is difficult to extract into methylene chloride at high recoveries. Moreover, the overall recovery of cyclobutanone is low (70–80%), and the authors fail to specify any methods for removing close-boiling impurities such as crotonaldehyde and cyclopropanecarboxaldehyde, as well as color bodies.

French Patent FR 0112261 discloses a process for the preparation of aldehydes or ketones in which molecular oxygen in conjunction with a bimetallic catalyst is used to oxidatively dehydrate primary or secondary, mono- or polyfunctional alcohols that contain two to thirty-six carbon atoms. The water formed is removed in the course of the reaction by azeotropic distillation using an organic solvent chosen in such a way that: (1) the binary azeotrope that the solvent forms with water has a boiling point of at least 50° C., (2) the boiling point of the solvent is less than the boiling point of the alcohol to be dehydrogenated, and (3) the boiling point of the solvent is less than the boiling point of any binary azeotrope that may form between the alcohol and water as well as the alcohol and the organic solvent itself. The organic solvent is specified to have a boiling point between 50° C. and 200° C. and is chosen from among aliphatic, cycloaliphatic, or aromatic hydrocarbons; alkyl or alkenyl esters of aliphatic carboxylic acids; aliphatic, aromatic, or cyclic ethers; aliphatic, cycloaliphatic, or aromatic nitriles; aliphatic, cycloaliphatic, or aromatic ketones. Furthermore, the azeotrope formed between water and the organic solvent must be heterogeneous.

Although FR 0112261 provides a general method for azeotropic distillative dehydration of ketones, the patent specifies that an additional solvent must be added to perform the dehydration of the ketone. Moreover FR 0112261 fails to contemplate methods for obtaining a high purity ketone product. No methods are disclosed for the removal of unreacted alcohol feed material, color bodies, other high and low boiling, or close-boiling impurities in order to obtain a high purity ketone product.

U.S. Pat. No. 2,647,861 discloses a process for the purification of ketones containing water and unreacted alcohol starting material, specifically for methyl ethyl ketone (MEK), methyl propyl ketone (MPK), and methyl butyl ketone (MBK) by two or three column pressure-swing distillation sequence. In the case of MEK, MPK, and MBK, the composition of the ketone-water azeotrope varies significantly with moderate changes in pressure. This patent also fails to contemplate methods for obtaining a high purity ketone product. No methods are disclosed for the removal of color bodies, other high- and low-boiling, or close-boiling impurities in order to obtain a high purity ketone product.

U.S. Pat. No. 2,684,934 discloses a process for the purification of mixtures of MEK and methyl isopropyl ketone containing water and unreacted ethanol and isopropanol by a combination of extractive distillation, extraction, and azeotropic distillation steps with an added solvent. The crude aqueous ketone-alcohol feed is first extractively distilled with water as the extractive distillation solvent. The column base product comprising unreacted ethanol, isopropanol and water is recycled to the ketone formation step, while the MEK-MIPK-water distillate product is counter-currently contacted with n-hexane in an extraction column. The water-rich raffinate comprising some MIPK and MEK is recycled to the extractive distillation column. The hexane-rich extractant, comprising most of the MIPK and MEK in the feed to the extractor, as well as some water, is fed to an azeotropic distillation column where the remaining water is taken overhead as the heterogeneous low-boiling ternary hexane-MEK-water azeotrope. The azeotrope is allowed to phase separate, is decanted, and the organic-rich layer containing most of the MEK and hexane is recycled to the extraction step. The aqueous layer of the decantation is recycled to the extractive distillation step. MEK and MIPK are then separated in a final distillation step.

U.S. Pat. No. 4,186,059 describes a similar solvent-assisted azeotropic distillation and extraction process for MEK dehydration using toluene as the water entrainer in the distillation step and hydrocarbon wax as the extraction solvent. French Patent FR 78 28329 teaches a similar azeotropic distillation processes for the dehydration of MEK using a light hydrocarbon as the water entrainer, preferably n-pentane. Soviet Union patent 1,567,603 teaches the use of diisopropyl ether as the solvent for MEK dehydration.

All of these MEK-related patents teach processes that are unduly complicated, expensive, and unnecessary for cyclobutanone dehydration. While MEK and water form a low-boiling heterogeneous azeotrope, the liquid-liquid region is small with high mutual solubility of MEK and water. Thus MEK is not a favorable entrainer for use in its own dehydration.

BRIEF SUMMARY OF THE INVENTION

We have developed a process for the recovery of cyclobutanone in a purity of at least 90 weight percent by a novel combination of distillation and processing steps. The purification process of the present invention involves a process for the recovery of cyclobutanone in a purity of at least 90 weight percent from a crude product mixture comprising cyclobutanone, water and a plurality of other organic compounds resulting from the oxidation of cyclobutanol in water by the steps comprising:

(1) distilling the crude product mixture to obtain (i) a distillate comprising cyclobutanone, water, cyclopropanemethanol, cyclobutanol, 3-butene-1-ol, 2-butene-1-ol, cyclopropanecarboxaldehyde, ethers and mixed ethers of cyclobutanol, cyclopropanemethanol, 3-butene-1-ol, and 2-butene-1-ol, and hemi-ketals and ketals of cyclopropanemethanol, cyclobutanol, 3-butene-1-ol and 2-butene-1-ol with cyclobutanone; and (ii) a distillation residue comprising water, metal salts, and high boiling organic compounds such as γ-butyrolactone, cyclopropane carboxylic acid, and hemi-ketals and ketals of cyclopropanemethanol, cyclobutanol, 3-butene-1-ol and 2-butene-1-ol with cyclobutanone;

(2) allowing the resultant mixture to separate into (i) an organic phase comprising a minor amount of the cyclobutanone contained in the distillate and a major amount of impurities less soluble in water than cyclobutanone such as ethers, ketals, and color bodies; and (ii) an aqueous phase comprising water, a major amount of the cyclobutanone contained in the distillate, a minor amount of more hydrophilic impurities such as alcohols and cyclopropane carboxaldehyde;

(3) distilling the aqueous phase from step (2) to obtain (i) a minor amount of distillate comprising low-boiling azeotropes comprising water and organic impurities in the aqueous phase, (ii) a major amount of distillate comprising an azeotrope of water and cyclobutanone, and (iii) a distillation residue comprising water, cyclopropanecarboxylic acid, γ-butyrolactone, cyclobutanol, cyclopropanemethanol, mixed ethers of the alcohols, and ketals formed from reactions between ethers and alcohols;

(4) allowing distillate (ii) from step (3) to separate into (i) a cyclobutanone-rich organic phase comprising cyclobutanone, water, and one or more aldehydes having boiling points close to that of cyclobutanone and (ii) an aqueous phase comprising cyclobutanone and water; and (5) distilling organic phase (i) from step (4) to obtain (i) a first distillate comprising an azeotrope of water and cyclobutanone, (ii) a second distillate comprising cyclobutanone having a purity of at least 90%, and (iii) a distillation residue comprising cyclobutanol, cyclopropanemethanol, mixed ethers of the alcohols, and ketals formed from reactions between ethers and alcohols.

The cyclobutanone product may contain an unacceptably high level of aldehydes, e.g., cyclopropanecarboxaldehyde and cis/trans-crotonaldehyde, since such compounds are particularly difficult to remove during the purification process. Thus, the 5-step purification process described above may include an aldehyde conversion step wherein the distillations of steps (3) and/or (5) are preceded with an aldehyde conversion wherein the material to be distilled in steps (3) and/or (5) is treated with a material which converts the aldehyde to another compound or compounds having boiling points higher than the otherwise difficult-to-separate aldehydes. This ancillary step causes the aldehyde(s) present to be converted to products which have higher boiling points and, therefore, are readily separated from the cyclobutanone.

Another variation of the present invention provides for the addition of an extraneous, inert (non-reactive), azeotrope-forming solvent to the material distilled is step (5). Yet another variation utilizes a pressure differential in the distillations of steps (3) and (5).

DETAILED DESCRIPTION

In the first step of the purification process provided by the present invention, crude aqueous cyclobutanone is distilled from a crude product mixture comprising cyclobutanone, water and a plurality of other organic compounds resulting from the oxidation of cyclobutanol in water. An example of the oxidation of cyclobutanol to cyclobutanone in water is described by Krumpolic and Rocek, supra, who oxidized cyclobutanol to cyclobutanone with chromium trioxide and oxalic acid in the presence of water. This crude product mixture typically comprises about 2 to 20 weight percent cyclobutanone, about 70 to 97 weight percent water and about 0.2 to 10 weight percent impurities including catalyst residues, unreacted cyclobutanol, and a plurality of by-products. The distillate from the first step comprises cyclobutanone, water, cyclopropanemethanol, cyclobutanol, 3-butene-1-ol, 2-butene-1-ol, cyclopropanecarboxaldehyde, ethers and mixed ethers of cyclobutanol, cyclopropanemethanol, 3-butene-1-ol, and 2-butene-1-ol, and hemi-ketals and ketals of cyclopropanemethanol, cyclobutanol, 3-butene-1-ol and 2-butene-1-ol with cyclobutanone. The distillation residue (undistilled material) comprises water, metal salts, e.g., chromium salts resulting from the use of a chromium compound in the synthesis of the cyclobutanone, high boiling organic compounds, e.g., γ-butyrolactone, ethers and mixed ethers of cyclobutanol, cyclopropanemethanol, 3-butene-1-ol, and 2-butene-1-ol, and hemi-ketals and ketals of cyclopropanemethanol, cyclobutanol, and heavy acids, e.g., oxalic acid, and cyclopropane carboxylic acid.

The first step is carried out by heating the crude oxidation mixture to its boiling point, followed by collection and condensation of evolved vapors. It is desirable for the first distallation step to remove essentially all of the cyclobutanone in the crude reaction mixture and effect a concentration the cyclobutanone in the vapor condensate. Many of the organic impurities present in the crude product mixture form low-boiling azeotropes with water and tend to be carried overhead with the cyclobutanone during the first step distallation. A number of these impurities are highly colored and cause coloration of the final cyclobutanone product if not removed effectively. However, we have found that these impurities generally are much less soluble in water than cyclobutanone. Although the binary system cyclobutanone-water separates into two liquid phases at concentrations above 20 weight percent cyclobutanone, a typical crude cyclobutanone condensate from the step (1) distallation will separate into two liquid phases at much lower concentrations of cyclobutanone, e.g., as low as about 1 to 2 weight percent cyclobutanone, because of the presence of hydrophobic impurities. Most of the cyclobutanone is present in the aqueous layer, whereas the more hydrophobic impurities tend to concentrate in the organic layer. In this fashion, many of the heavy impurities can be removed readily from the crude aqueous cyclobutanone mixture before further distallation, while still maintaining high recovery of cyclobutanone.

The concentration of cyclobutanone in the condensed distillate from step (1) typically is in the range of 2 to 20 weight percent, preferably about 4 to 12 weight percent, based on the total weight of the condensed distillate. This concentration range maximizes cyclobutanone recovery into the aqueous phase, while minimizing co-extraction of impurities. If necessary, the concentration of cyclobutanone in the condensed distillate may be adjust to about 2 to 20 weight percent, preferably about 4 to 12 weight percent, by the addition of fresh water. Generally one or more equilibrium separation stages is sufficient to achieve the desired concentration in the flash distillation step.

The organic and aqueous phases formed upon condensation of the distillate from the first step are separated and the aqueous layer is retained for subsequent distillative purification steps. The organic layer may be further extracted with fresh water, either in cross-flow or multi-stage countercurrent extraction modes, to extract additional cyclobutanone from the undesired impurities, improving the recovery rate. Typically 1 to 8 stages, more preferably 2 to 6 stages, of cross-flow or countercurrent extraction is sufficient to recover most of the cyclobutanone from the organic phase. The preferred water to organic phase weight ratio is in the range of about 1:4 to 5:1, more preferably about 0.5:1 to 2:1. All of the aqueous extract phases from each extraction step are combined with the aqueous layer from distillation step (1) for subsequent recovery and purification of cyclobutanone. The raffinate phase, containing primarily organic impurities, is discarded as a waste stream.

The aqueous layer from the flash distillation step is further processed in a two-step, azeotropic distillation sequence with an intermediate decantation step, i.e., steps (3), (4) and (5) described above. This distillation sequence serves to remove water, alcohols, high and low boilers, and is capable of producing cyclobutanone having a purity equal to or greater than 90 weight percent, preferably greater than 95 weight percent, most preferably greater than 99 weight percent. Cyclobutanone itself is used as a dehydrating agent to remove water from the mixture. The two-column sequence may be operated in either batch or continuous mode with equal efficacy.

In the third step of our novel purification process, the aqueous phase from the first distillation step is charged to a first still pot and distilled to first give a minor amount of distillate which is collected to remove lowing boiling compounds and low-boiling organic-water azeotropes. The fore-cut typically is 0.1 to 0.6 weight percent, more typically 0.1 to 0.3 weight percent, of the initial charge to the still pot. The head temperature will typically be 2 to 4° C. less than the boiling point of the cyclobutanone-water azeotrope while collecting the forecut. The actual head temperature, of course, depends on the operating pressure of the column. Thus, for example, at 740 torr, the head temperature will be about 78 to 81° C.

When the head temperature of the step (3) distillation column approaches, e.g., is less than about 2° C. from the boiling point of the cyclobutanone-water azeotrope, collection of the product fraction, i.e., distillate (ii) of step (3), is begun. The composition of the product cut is essentially that of the water-cyclobutanone azeotrope. i.e., approximately 80 weight percent cyclobutanone. Collection of this product fraction is continued until cyclobutanone is substantially depleted from the still pot. While the cyclobutanone-water azeotrope is being distilled overhead, the head temperature of the distillation column will remain essentially constant at the boiling point of the cyclobutanone-water azeotrope. Thus, for example, at about 740 torr column pressure the head temperature will be about 82–83° C. If the distillation is continued after the head temperature has risen significantly above that of the cyclobutanone-water azeotrope, higher boiling impurities, e.g., cyclobutanol and cyclopropanemethanol and substantial quantities of water will be distilled overhead and will contaminate the distillate product cut. It is preferable to stop the distillation after the head temperature has risen from 1 but not more than 15° C., more preferably from 2 to not more than 8° C., most preferably from 2 to not more than 5° C., above the boiling point of the cyclobutanone-water azeotrope at the column operating pressure.

The distillation residue (iii) from step (3) typically contains high-boiling impurities such as cyclopropanecarboxylic acid, γ-butyrolactone, cyclobutanol, cyclopropanemethanol, mixed ethers of the alcohols, and ketals formed from reactions between ethers and alcohols as well as any remaining cyclobutanone. It is advantageous to operate the first azeotropic distillation step in a column with sufficient equilibrium staging and reflux to separate substantially the alcohol-water azeotropes from the cyclobutanone-water azeotrope. If these impurities are allowed to co-distill with the cyclobutanone, then they tend to accumulate in the bottoms of the second distillation column. High concentrations of alcohols, e.g., cyclobutanol and cyclopropanemethanol, in the base of the second column promote losses of cyclobutanone to hemi-ketals and ketals, and well as lead to water evolution. Stringent water specifications for the product cyclobutanone are then difficult to meet. The column should contain at least 5 equilibrium stages, more preferably at least 10 equilibrium stages if cyclobutanol and cyclopropanemethanol levels in the feed to the column are low, i.e., less than 0.005 weight percent. The column should contain at least 10 equilibrium stages, more preferably at least 15 equilibrium stages, if cyclobutanol and cyclopropanemethanol levels in the feed to the column are high, i.e., greater than 0.005 weight percent. The preferred reflux ratio depends, of course, on the number of equilibrium stages and concentration of alcohols, but a ratio of 2:1 to 10:1, preferably 2:1 to 7:1 usually is adequate. The distillation may be carried out at constant reflux ratio throughout or may be operated with a variable reflux policy in a manner well known in the art. If sufficient staging and an adequate reflux ratio are provided, most of the alcohols and other heavy impurities can be separated effectively, and left with the water remaining in the still pot. Typical operating pressures are about 100 to 3000 torr (0.013 to 0.4 Mpa), preferably about 380 to 1520 torr (0.05 to 0.2 MPa).

Step (3) has been described above in the context of batch operation. However, it will be apparent to those skilled in the art that step (3) may be carried out in a continuous mode wherein distillates (i) and (ii) and residue (iii) are removed simultaneously from a distillation column. For example, continuous operation of step (3) may comprise feeding the aqueous phase from step (2) to a distillation column and removing from the column (i) a minor amount of distillate, e.g., from the side of the upper section of the column, comprising low-boiling azeotropes comprising water and organic impurities in the aqueous phase, (ii) a major amount of distillate, e.g., from the top or upper section of the column, comprising an azeotrope of water and cyclobutanone, and (iii) a column underflow product, i.e., a liquid distillation residue removed from the base of the column, comprising water, cyclopropanecarboxylic acid, γ-butyrolactone, cyclobutanol, cyclopropanemethanol, mixed ethers of the alcohols, and ketals formed from reactions between ethers and alcohols.

If sufficient staging and an adequate reflux ratio are provided so that the composition of the product cut is essentially that of the cyclobutanone-water azeotrope, then the product cut will separate readily into two liquid phases.

The upper organic phase, i.e. phase (i) of step (4), comprising about 96 weight percent cyclobutanone, about 4 weight percent water and less than about 1 to 2 weight percent organic impurities is subjected to further processing in step (5). The bottom water phase, i.e., phase (ii) of step (4), comprising about 20 weight percent cyclobutanone, may be recycled to subsequent step (3) distillations to increase overall cyclobutanone recovery or it may be discarded as desired. It is preferable to recycle the aqueous layer.

Step (5) of our novel process involves distilling organic phase (i) from step (4) to obtain cyclobutanone having a purity of at least 99%, preferably at least 99.5%. In step (5), a first distillate fraction is collected at a column head temperature approximately that of the boiling point of the cyclobutanone-water azeotrope. Thus, for example, at about 740 torr column pressure, the head temperature will be about 82–83° C. The composition of the first distillate fraction is essentially that of the water-cyclobutanone azeotrope (approximately 80 weight percent cyclobutanone). The first distillate fraction will separate into two liquid phases upon standing. The aqueous layer may be recycled to step (3) and the organic layer to step (5). Collection of the first distillate fraction is continued until water is depleted substantially from the material fed to the still pot, e.g., water is depleted until the material fed to the still pot contains less than about 1 weight percent, preferably less than 0.5 weight percent, more preferably less than 0.3 weight percent water. As the water content of the material being distilled drops below the composition of the cyclobutanone-water azeotrope, the column head temperature gradually rises toward the boiling point of pure cyclobutanone, i.e., 98–99° C. at 760 torr.

When the column head temperature closely approaches, i.e., is less than about 1° C. from, the boiling point of pure cyclobutanone, collection of the product cut is begun. The composition of the product cut is essentially that of pure cyclobutanone. While the cyclobutanone product is being distilled overhead, the head temperature of the still will remain essentially constant at the boiling point of pure cyclobutanone. Thus, for example, at about 740 torr column pressure, the head temperature will be about 96–97° C. If the distillation is continued after the head temperature has risen substantially above that of pure cyclobutanone, then the higher boiling impurities, e.g., cyclobutanol, cyclopropanemethanol, ketals, and ethers will be carried overhead and will contaminate the distillate product fraction. It is preferable to stop the distillation after the head temperature has risen from about 0.1 but not more than 6° C., more preferably from about 0.2 but not more than 4° C., most preferably from about 0.2 to not more than 2.5° C., above the boiling point of pure cyclobutanone at the column operating pressure.

The step (5) distillation column should contain at least 8 equilibrium stages, more preferably at least 12 equilibrium stages. The preferred reflux ratio depends, of course, on the number of equilibrium stages, but a ratio of 2:1 to 12:1, preferably 2:1 to 8:1, is generally adequate. The distillation may be carried out at constant reflux ratio throughout or may be operated with a variable reflux policy in a manner well known in the art. Typical operating pressures are 100 to 3000 torr (0.013 to 0.4 MPa, More typical pressures are 380 to 1520 torr (0.05 to 0.2 MPa). If sufficient staging and an adequate reflux ratio are provided, and other aspects of this invention are followed, cyclobutanone product purities of greater than 90 weight percent, more typically greater than 95 weight percent, and most preferably greater than 99 weight percent, are readily achievable.

The residue in the pot typically comprises unrecovered cyclobutanone as well as high boiling impurities such as cyclopropanecarboxylic acid, γ-butyrolactone, cyclobutanol, cyclopropanemethanol, mixed ethers of the alcohols, and ketals formed from reactions between ethers and alcohols. We have found it advantageous to recycle the still pot residue from step (5) to subsequent step (3) distillations rather than as feed to subsequent step (5) distillations. In this fashion, cyclobutanol and cyclopropanemethanol are not allowed to build up to appreciable levels in the still pot of step (5) distillation, i.e., greater than about 2–3 weight percent. High concentrations of alcohols in the dehydrating environment in the base of the second column promote losses of cyclobutanone to hemi-ketals and ketals, and well as lead to water evolution. High recovery and stringent water specifications for the product cyclobutanone are then difficult to meet. Separation of the alcohols from cyclobutanone is best done in the presence of large excesses of water, i.e., in the step (3) distillation, to shift the hemi-ketal/ketal equilibrium toward cyclobutanone/alcohol rather than ketal.

Although the process provided by the present invention is described in detail herein as a batch operation, it will be apparent to those skilled in the art that it can be operated in a continuous mode.

If the aldehyde levels in organic phase (i) of step (4) are above the desired purity specification of the cyclobutanone product, the removal of some or all of such aldehydes is necessary prior to the step (5) distillation. Normally, the aldehyde content of the cyclobutane product should be less than about 2 weight percent, preferably less than about 0.5 weight percent, more preferably less than about 0.2 weight percent. Aldehydes which are particularly difficult to separate by distillation are cyclopropanecarboxaldehyde and cis/trans-crotonaldehyde. These aldehydes boil within a few degrees of cyclobutanone and are extremely difficult to remove economically by distillation. Thus, it is desirable to remove them by other means. The preferred means is via chemical conversion to high-boiling species that are easily separable by distillation. We have discovered that close-boiling, aldehyde impurities can be converted to high boiling, easily distillable compounds by oxidation with molecular oxygen or a molecular oxygen-containing gas such as air, or via condensation reactions catalyzed by amines or inorganic bases.

The close-boiling aldehyde impurities can be converted readily to high-boiling acids under mild conditions by contacting organic phase (i) of step (4) with a molecular oxygen- containing gas such as oxygen, air or oxygen-enriched air. Thus, molecular oxygen or air may be bubbled through the aldehyde-containing mixture and held at an oxidation temperature for a given contacting time. Typical conditions for the oxidation are 4 to 120 hours hold time at 20 to 80° C., more typically 15 to 60 hours at 40 to 60° C. The oxidation reaction is highly selective toward the oxidation of the aldehyde and losses of the ketone normally are significantly less than 1 percent of the initial charge.

It is well known in the art that other oxidants, e.g., peroxidants, will convert aldehydes to acids, but we have found these compounds to be disadvantaged in our invention. Peroxy acids such as peracetic acid are not preferred because they are non-selective and destroy large amounts of cyclobutanone as well the aldehydes. Although aldehydes are highly reactive toward peroxy acids, in the presence of the large excess of cyclobutanone over the aldehydes, the formation of the lactone, γ-butyrolactone, tends to predominate over formation of acids from the aldehydes. For similar reasons hydrogen peroxide or organic hydroperoxides, such as tert-butyl hydroperoxide, are not preferred.

A second method of converting the aldehyde to readily distillable compounds is via base-catalyzed, aldol-type condensation reactions. A catalytic amount of base, e.g., 0.1 to 1 stoichiometric equivalents based on the amount of aldehyde present, is added to organic phase (i) of step (4). The aldehyde-containing mixture is heated and held at temperature for a given time period. Typical conditions for the condensation reaction are a reaction time of 2 to 75 hours at 20 to 80° C., more typically 15 to 50 hours at 40 to 60° C. During the reaction time the more reactive aldehydes are converted to high-boiling condensation products while only a small fraction of the cyclobutanone participates in similar condensation reactions.

Preferred bases are secondary and tertiary amines, inorganic bases, and basic resins, particularly those with secondary amine functionality. Weaker bases, although reducing the rate of reaction, are more selective toward aldehyde over ketone condensation and are thus preferred. The preferred bases have a pKa less than 11, more preferably less than 10.5. The preferred secondary and tertiary amines include di- and tri-alkyl amines wherein the alkyl groups are selected from alkyl containing from about 1 to 20, preferably about 2 to 10, carbon atoms and hydroxyalkyl groups containing 2 to about 4 carbon atoms. A particularly preferred base is diethanolamine. Primary amines such as n-butylamine not preferred because they are non-selective and destroy a large fraction of cyclobutanone as well the aldehydes. Although aldehydes are highly reactive toward base catalyzed condensation reactions, in the presence of the large excess of cyclobutanone over the aldehydes, the formation of the ketone-derived imine tends to predominate over formation of aldol condensation products of the aldehydes.

Since the base acts as a catalyst rather than a reagent, the base will continue to catalyze condensation reactions, particularly undesirable cyclobutanone condensation reactions, during the final distillation step. This tendency to continue catalysis of cyclobutanone condensation is particularly pronounced at the high temperatures and dry environment of the distillation reboiler or still pot. Thus, it is critical for high yields of cyclobutanone to either remove or neutralize the base before the final distillation step or to remove it rapidly during the second distillation. If the base catalyst is lower boiling than the cyclobutanone-water azeotrope or forms an azeotrope with water that has a boiling point lower than the cyclobutanone-water azeotrope, then the base can be removed rapidly from the still pot in step (5), e.g., as a part of first distillate (i) of step (5). For example, diisopropylamine forms a minimum-boiling azeotrope with water with a boiling point of 74° C. and, therefore, can be removed via distillation as a component of first distillate (i) of step (5). The amount of first distillate which comprises an azeotrope of low-boiling amine and water typically is about 0.2 to 3.0 weight percent, more typically 0.5 to 2.0 weight percent, of the material distilled in step (5). The column head temperature typically will be close to the boiling point of the amine-water azeotrope while collecting the forecut. The actual head temperature, of course, depends on the operating pressure of the column. Thus, for example, at 740 torr, the head temperature will be about 73–74° C. with diisopropylamine as the base catalyst. It is preferable that the boiling point of the amine or the amine-water azeotrope is at least 8° C., more preferably at least 15° C. less than the boiling point of the cyclobutanone-water azeotrope.

The base catalyst, particularly higher-boiling bases that cannot be removed by distillation, may be neutralized by addition of acid, but precise titration is difficult. Use of too little acid for complete neutralization does not ameliorate the catalytic action of the remaining base, while use of too much acid promotes undesirable acid-catalyzed ketal and ether formation reaction in the subsequent final distillation step. We have discovered that the base can be removed effectively from the cyclobutanone mixture by treatment with a strong acid-form resin, e.g., an acidic, ion exchange resin bearing sulfonic acid groups. The acid resin may be contacted with the base-containing mixture either as a slurry of the resin powder or in a packed bed of the resin. If the resin is slurried, it may be recovered from the mixture by filtration methods well known in the art. A preferred acid resin is hydrogen-form Amberlyst 15 resin. Many other resins of similar configuration will function effectively for base removal.

A high-boiling solvent (solvent I) optionally may be added to the feed of distillation step (5) to provide a heel or residue for the distillation to improve heat transfer and cyclobutanone recovery. This solvent I should have the following characteristics: (1) a boiling point significantly above, e.g., at least 30° C., the boiling point of cyclobutanone; (2) does not form a binary azeotrope with cyclobutanone; (3) does not form a binary azeotrope with alcohol contaminants that has a boiling point close to the boiling point of pure cyclobutanone, e.g., within about 10° C.; and (4) is non-reactive with cyclobutanone. Examples of such high-boiling, inert solvents I are high-boiling, straight and branched chain alkanes and alkyl esters of alkanoic-acids such as n-decane, n-nonane, and isobutyl isobutyrate. Mixed solvents having these characteristics also are useful for this aspect of the invention. The inert auxiliary solvents I typically have a boiling point of at least 130° C., preferably about 140 to 200° C. The amount of the optional, high-boiling solvent I which may be used typically will be in the range of about 0.1 to 2 parts by weight based on the weight of the feed material for the distillation of step (5).

Another variation of the process provided by the present invention utilizes an extraneous solvent (solvent II) in step (5). The extraneous solvent II is selected to provide a ternary system consisting of cyclobutanone, water, and the extraneous solvent II having the following characteristics:

(1) The solvent forms a heterogeneous, minimum-boiling, binary azeotrope with water or a heterogeneous, ternary, minimum-boiling, azeotrope with water and cyclobutanone that is the lowest boiling of all binary azeotropes and pure components in the ternary system; and (2) The solvent is non-reactive with cyclobutanone.

The inert, extraneous solvent II preferably does not form a binary azeotrope with alcohol contaminants that has a boiling point close to the boiling point of pure cyclobutanone, i.e., within about 10° C. The organic solvent II preferably is selected from aliphatic, cycloaliphatic, and aromatic hydrocarbons containing up to about 7 carbon atoms; aliphatic, aromatic, and cyclic ethers containing up to about 6 carbon atoms; aliphatic, and cycloaliphatic nitriles containing up to about 5 carbon atoms; and aliphatic and cycloaliphatic ketones containing up to about 6 carbon atoms, aliphatic and cycloaliphatic halogenated hydrocarbons containing up to about 6 carbon atoms and up to about 3 chlorine, or 6 fluorine, or 3 bromine atoms, and aliphatic or cycloaliphatic esters containing up to about 5 carbon atoms. Specific examples of the inert, extraneous solvents II include methyl tert-butyl ether (MTBE), tert-amyl-ether, ethyl acetate, isopropyl acetate, n-pentane, n-hexane, cyclohexane, methyl isopropyl ketone, 1-chlorobutane, and 2-chlorobutane.

When using inert, extraneous, organic solvent II in distillation step (5), a first distillate fraction is collected at a column head temperature approximately that of the boiling point of the solvent II-water binary azeotrope or the solvent II-water-cyclobutanone ternary azeotrope. Thus, for example, with MTBE as the solvent II and with a column pressure of about 740 torr, the head temperature will be about 51–52° C. The composition of first distillate (i) is comprised essentially of the binary or ternary azeotrope with the solvent II. First distillate (i) will separate into two liquid phases upon standing. The aqueous phase may be recycled to subsequent step (3) distillations, and the organic phase to subsequent step (5) distillations. Collection of first distillate (i) is continued until substantially all of the water is depleted from the still pot. As the water content of the still drops below the composition of the binary or ternary azeotrope with the solvent, the head temperature will gradually rise toward the boiling point of the extraneous solvent II. The next distillate fraction comprising water, cyclobutanone, and solvent II, is taken as the last traces of water and any excess solvent II are distilled overhead. This fraction also may be recycled to subsequent step (3) distillations. When the column head temperature closely approaches, i.e., is less than about 1° C. from, the boiling point of pure cyclobutanone, collection of the product fraction (ii) is begun as described above.

The amount of extraneous, inert solvent II added to the feed material distilled in step (5) is based on the water content of the feed material. Normally, sufficient solvent II is charged to the still pot to give an excess, preferably a 5 to 30% excess, with respect to the composition of the binary solvent II-water azeotrope or ternary water-solvent II-cyclobutanone azeotrope. Thus, for example, if MTBE is used as the solvent II, the composition of the binary MTBE-water azeotrope is 4 weight percent water. Thus, MTBE is added at a rate of at least 24 kg of MTBE per kg of water in the feed, more typically 25.2 to 36 kg MTBE per kg of water.

In yet another variation of our invention, the step (3) and step (5) distillations are carried out using different pressures. In this embodiment of our invention, described herein as operated in a continuous-feed mode, the separation operation specified above in step (4) is not essential to the successful operation of the overall process to recover cyclobutanone having a purity of 90% or greater. However, the step (4) separation may be included in the operation of the process. This embodiment of out invention thus consists of a process for the recovery of cyclobutanone in a purity of at least 90 weight percent from a crude product mixture comprising cyclobutanone, water and a plurality of other organic compounds resulting from the oxidation of cyclobutanol in water by the steps comprising:

I. distilling the crude product mixture to obtain (i) a distillate comprising cyclobutanone, water, cyclopropanemethanol, cyclobutanol, 3-butene-1-ol, 2-butene-1-ol, cyclopropanecarboxaldehyde, ethers and mixed ethers of cyclobutanol, cyclopropanemethanol, 3-butene-1-ol, and 2-butene-1-ol, and hemi-ketals and ketals of cyclopropanemethanol, cyclobutanol, 3-butene-1-ol and 2-butene-1-ol with cyclobutanone; and (ii) a distillation residue comprising water, metal salts, and high boiling organic compounds such as comprising γ-butyrolactone, cyclopropanecarboxylic acid, and hemi-ketals and ketals of cyclopropanemethanol, cyclobutanol, 3-butene-1-ol and 2-butene-1-ol with cyclobutanone;

II. allowing the resultant mixture to separate into (i) an organic phase comprising a minor amount of the cyclobutanone contained in the distillate, a major amount of impurities less soluble in water than cyclobutanone such as ethers, ketals, and color bodies; and (ii) an aqueous phase comprising water, a major amount of the cyclobutanone contained in the distillate, a minor amount of more hydrophilic impurities such as alcohols and cyclopropane carboxaldehyde;

III. distilling the aqueous phase from step II at a pressure in the range of 100 to 2000 torr to obtain (i) a condensed distillate product comprising an azeotrope of water and cyclobutanone and (ii) a column underflow product comprising water, cyclopropanecarboxylic acid, γ-butyrolactone, cyclobutanol, cyclopropanemethanol, mixed ethers of the alcohols, and ketals formed from reactions between ethers and alcohols; and IV. distilling distillate (i) from step III at a pressure of about 2000 to 6000 torr to obtain (i) a distillate product comprising an azeotrope of water and cyclobutanone which is recycled to the feed of step III distillation and (ii) a column underflow product comprising cyclobutanone having a purity of at least 90%;

provided the step IV distillation is operated at a pressure at least 760 torr greater than the pressure at which step III is operated.

Distillation step III is operated at a pressure of 100 to 2000 torr (0.013 to 0.26 MPa), preferably 700 to 1250 torr (0.093 to 0.17 MPa). The condensed distillation product from the step III distillation, optionally after destruction of close-boiling aldehydes, is fed for final purification of the cyclobutanone to the step IV distillation column at a higher pressure than the distillation step III. The step IV distillation column is operated at a pressure substantially above, e.g., at least 760 torr (0.1 MPa), more preferably at least 2280 torr (0.3 MPa) above, the pressure of the step III distillation column. The step IV distillation column typically is operated at pressures of about 2000 to 6000 torr (0.26 to 0.8 MPa, more typically at pressures of about 3500 to 5500 torr (0.4 to 0.53 MPa). If sufficient staging and an adequate reflux ratio are provided, and other aspects of this invention are followed, cyclobutanone product purities of greater than 90 weight percent, more typically greater than 95 weight percent, and most preferably greater than 99 weight percent, are readily achievable.

Our novel process is further illustrated by the following examples. The percentages set forth in the examples are by weight unless otherwise specified.

Preparation of Crude Cyclobutanone Product

A 50-liter, round-bottom, glass flask was equipped with an electrical heating mantle, air-driven stirring motor, and thermocouple. One neck of the flask was fitted with a short, unpacked, glass column having a length of 0.61 meters (2 feet), a distillation head, water-cooled condenser, and was connected to a 5-liter drop-bottom receiving flask. Both the receiver and reaction flask were blanketed with nitrogen and equipped with a dry ice vent trap. The reaction flask was charged with 5750 grams of water. The air-driven stirrer was started and 1315 grams of concentrated hydrochloric acid and 1140 grams of cyclopropanemethanol was added to the flask. The mixture was heated to reflux and held at temperature for 4 hours. The mixture was cooled to 30° C. and transferred to an ice-cooled jacketed, 50-liter, round bottom flask fitted with an air-driven stirring motor, thermocouple, nitrogen purge line and dry ice vent condenser. While stirring, 0.9 liters of water was added to the ice-cooled flask, followed by 3961 g of oxalic acid. The reaction was allowed to cool to 25° C. and a mixture of 3148 grams of chromium trioxide in 4860 grams of water was added drop-wise to the jacketed flask over a period of 10 hours, while maintaining the temperature at 25° C. Upon completion of the addition of the aqueous chromium trioxide, the reaction mixture was stirred for one hour at 25° C.

EXAMPLE 1

Step (1) Distillation

The crude cyclobutanone product prepared as described above was transferred to a 50-liter round bottom distillation flask and heated to the boiling point. Over the course of 24 hours of operation at total take-off, approximately 3881 grams of step (1) distillate product were collected in the receiver. The step (2) material in the receiver separated into two liquid phases. The small, highly-colored, upper organic phase (i) was comprised of about 50% cyclobutanone. The crude aqueous phase (ii) was comprised of 8.8% cyclobutanone. Thus, no water addition was required to adjust the cyclobutanone concentration to the preferred range. Although variations are possible, the concentration of cyclobutanone in aqueous layer (ii) typically is 3 to 20% of original organic layer had been recovered into the combined extract streams. Even higher recoveries of cyclobutanone are possible if larger amounts of water or more extraction stages are used. The distribution coefficient for cyclobutanone is typically an order of magnitude higher than that for the impurities thus showing that water is a very selective extraction solvent for cyclobutanone versus the impurities.

TABLE I

| Extraction | Organic Phase | | | | Aqueous Phase | | | | Cumulative Recovery | | Distribution Coefficient | |
|---|---|---|---|---|---|---|---|---|---|---|---|---|
| | Composition | | | | Composition | | | | | | | |
| No | Weight | $H_2O$ | CBON | Imp | Weight | H2O | CBON | Imp | CBON | Imp | CBON | Imp |
| 1 | 84.3 | 2.75 | 55.34 | 41.92 | 114.3 | 88.91 | 10.31 | 0.79 | 20 | 2.5 | 0.186 | 0.019 |
| 2 | 71.99 | 2.21 | 51.09 | 46.70 | 95.1 | 88.94 | 9.15 | 1.91 | 35 | 7.6 | 0.179 | 0.041 |
| 3 | 61.74 | 2.07 | 44.62 | 53.31 | 80.8 | 88.74 | 8.70 | 2.55 | 47 | 13.4 | 0.195 | 0.048 |
| 4 | 53.8 | 1.62 | 37.48 | 60.90 | 67.4 | 90.96 | 8.81 | 0.24 | 57 | 13.8 | 0.235 | 0.004 |
| 5 | 47.34 | 0.00 | 31.99 | 68.01 | 59.8 | 91.94 | 7.68 | 0.38 | 65 | 14.5 | 0.240 | 0.005 |
| 6 | 42.32 | 1.36 | 26.07 | 72.57 | 50.9 | 93.29 | 6.31 | 0.40 | 70 | 15.0 | 0.242 | 0.005 |
| 7 | 38.4 | 1.39 | 21.99 | 76.62 | 44.6 | 93.99 | 5.64 | 0.37 | 75 | 15.5 | 0.257 | 0.005 |
| 8 | 34.7 | 1.09 | 16.32 | 82.59 | 40.7 | 92.60 | 4.23 | 3.17 | 78 | 19.1 | 0.259 | 0.038 | the solution, more typically 6 to 15%. Organic layer (i) may contain up to about 95% cyclobutanone, more typically 30 to 85% cyclobutanone.

EXAMPLE 2

Step (2) Water Extraction of Organic Phase (i) of Step (1) Distillate

Cross flow extraction experiments were performed on organic phase (i) obtained from the step (1) distillation described above to demonstrate that: (1) further cyclobutanone can be recovered from organic phase (i) and (2) water is a selective solvent for separating cyclobutanone from other oxidation by-products. Organic phase (i) consisted of approximately 5% water, 59% cyclobutanone and 36% organic impurities.

A series of cross-flow extraction experiments were performed on a portion of the small organic phase (i) layer obtained from the step (1) distillation by the following procedure: Organic phase (i) was charged to a separatory funnel along with an equal mass of demineralized water. The funnel was shaken for two minutes and then the phases were allowed to separate. The resulting aqueous and organic phases were decanted and each phase was analyzed by GC. The new organic phase so obtained from the first extraction was then combined with an equal mass of fresh demineralized water once again for the second extraction and so on for a total of eight cross flow extractions. Because it was not possible to identify all of the impurities individually, a response factor of unity for the thermal conductivity (TC) detector was assumed for the impurities and the weight percents for water, cyclobutanone, and impurities was normalized to 100%.

Phase compositions and distribution coefficients for the series of eight cross-flow extractions are given in Table I wherein the weights of the organic (or raffinate) phase and the aqueous (or extract) phase are given in grams, CBON is cyclobutanone, Imp represents the impurities present, and the values given for the composition of the organic and aqueous phases and the cumulative recoveries are weight percentages. The distribution coefficient is defined as the mass fraction of a given component in the water (extract) phase divided by the mass fraction of the same component in the organic (raffinate) phase. After eight extractions, 78% of the cyclobutanone and only 19% of the impurities in the

EXAMPLE 3

Step (3) Distillation

Approximately 789 kg (1740 pounds) of aqueous phase (ii) prepared by the above described Step (1) Distillation procedure was charged to a 5003.8 liter (500 gallon), glass-lined reactor equipped with a packed, 6.1 meter×25.4 cm diameter (20-foot×10-inch diameter) column, a reflux splitter, condenser, and receiver vessel. The composition of the initial charge was ~9% cyclobutanone and 0.25% cyclopropanecarboxaldehdye. The reactor vessel was heated with steam and held at total reflux until the column head temperature reached about 80° C. The reflux ratio was switched to 6/1 to begin collection of distillate cuts. With the head temperature between 81.8–82° C., a small distillate forecut was collected to remove low-boilers from the system. The forecut weighed approximately 2.9 kg (6.39 pounds) or 0.4% of the initial charge, comprising approximately 1.9 kg (4.13 pounds) of cyclobutanone. The product fraction was collected at a reflux ratio of 6/1, with the column head temperature between 81.9 and 85° C. The product fraction weighted 81.6 kg (180 pounds) and contained 78.5% cyclobutanone, approximately the composition of the cyclobutanone-water azeotrope, and 0.35% cyclopropanecarboxaldehyde. The vessel was cooled and 702.3 kg (1548.5 pounds) of material containing 0.4% cyclobutanone were drained from the still pot. Cyclobutanone recovery was 97% of the feed charge, with 95% accountability. This experiment clearly demonstrates that cyclobutanone can be concentrated readily to the azeotropic composition, but that cyclobutanone cannot be fractionated effectively from cyclopropanecarboxaldehdye.

EXAMPLE 4

Step (4) Separation

The product fraction from the Step (3) Distillation described above was allowed to separate into two liquid phases. The bottom, aqueous layer [aqueous phase (ii)], weighing 19.5 kg (43 pounds) and containing 18% cyclobutanone, was drained from the receiver and retained for recycle. The upper organic layer [organic phase (i)], weighing 62.1 kg (137 pounds) and containing 94.5% cyclobutanone and 0.35% cyclopropanecarboxaldehyde, was retained for further purification.

EXAMPLE 5

Step (5) Distillation

Approximately 64.6 kg (142.5 pounds) of organic phase (i) prepared by the above-described procedures was charged to a 100-liter glass still pot equipped with a 1.37-m×15.2-cm (54-inch×6-inch) diameter column packed with 6.35 mm (025-inch) HC-276 Penn State random packing, a reflux splitter, condenser, and receiver vessels. The feed material was not treated with the optional aldehyde destruction step. The still pot was heated with steam and held at total reflux until the head temperature reached about 81.7° C. The reflux ratio was switched to 6/1 to begin collection of the first distillate fraction. As the cyclobutanone-water azeotrope distilled from the pot, the head temperature remained constant at about 82° C. When the water inventory in the column fell below the azeotrope composition, the temperature began to rise rapidly, leveling off at about 98° C. This fraction [first distillate (i)] weighed 22.7 kg (50 pounds) of material containing 80% cyclobutanone. It was retained for recycle to subsequent Step 3 Distillations.

At this point of the Step 5 Distillation the water essentially was depleted from the still and product collection began. The distillation was continued until the base jacket temperature reached 143° C. and the head temperature was at 99° C. A total of approximately 30.8 kg (68 pounds) of product fraction [second distillate (ii)] was collected. The product fraction contained 99.17% cyclobutanone, 0.15% water, 0.57% cyclopropanecarboxaldehyde, 0.04% butyrolactone, with no detectable cyclopropanemethanol or cyclobutanol. The still pot residue [distillation residue (iii)] weighed 8.4 kg (18.5 pounds) and was comprised of approximately 0.3% cyclopropanemethanol, 0.04% water and about 5% unidentified heavy ends. This material was retained for recycle to Step (3) Distillation.

EXAMPLE 6

Step (3) Distillation

An aqueous mixture containing 13.2% cyclobutanone and 0.7% cyclobutanol obtained by the step (1) distillation and step (2) separation described in Examples 1 and 2 was charged to a 2-liter, glass, round-bottom flask fitted with a 2.5-cm (1-inch) inside diameter, vacuum-jacketed, 20-plate Oldershaw column, liquid dividing head, reflux timer, and cooling water condenser. The column was operated in batch mode at a reflux ratio of 6/1. Approximately 0.2% of the charge to the still pot was collected as distillate (i) comprising low boilers, water, and some cyclobutanone at a column head temperature of 79–80° C. The main product [distillate (ii)] fraction was collected at a head temperature between 81.1° C. and 85° C. Distillate (ii) separated into two liquid phases having an overall composition of about 80% cyclobutanone, 20% water and less than 0.1% cyclobutanol. A final distillate fraction collected at a head temperature greater than 85° C. contained high levels of cyclobutanol, e.g., greater than 2%, and was kept segregated from the primary product cut. The still pot residue [distillation residue (iii)] was found to contain 0.9% cyclobutanol and less than 1% cyclobutanone. Overall recovery of cyclobutanone in the primary product cut was 92%. This example shows that cyclobutanol can be separated effectively from cyclobutanone by careful control of separation staging, reflux ratio, and column head temperature.

EXAMPLE 7

Step (4) Separation

The main product cuts of several step (3) distillations, carried out as in Example 6, were poured into a 500 ml separatory funnel. Total mass was 346.65 grams. The mixture was allowed to phase separate. The bottom water phase (68.6 grams), comprising about 21% cyclobutanone, was decanted and retained for recycle. The upper organic phase (265.3 g) comprised about 92% cyclobutanone and 7.0% water.

EXAMPLE 8

Step (5) Distillation

A portion, 254.5 grams, of the organic layer obtained in Example 7 was charged to the base pot of a batch distillation apparatus. The distillation apparatus comprised a 500-milliliter, round-bottom flask connected to an 2.5-cm (1-inch) inside diameter, vacuum-jacketed, glass column fitted with a liquid dividing head, reflux timer, cooling water condenser, distillate receiver flask, nitrogen blanketing line, and dry ice cold trap. The column was packed with 1 meter (40 inches) of 3.2-mm Penn State packing. After reaching steady state at total reflux, the reflux timer was set to 16% take-off and product collection was commenced. An initial distillate fraction [first distillate (i)], consisting of 62.4 grams of material, was collected while the distillation head temperature remained constant at about 82° C. This material separated into two liquid phases in the receiver flask and was found by gas chromatography to have a composition of essentially the water-cyclobutanone azeotrope (about 80% cyclobutanone in the combined aqueous and organic layers). At this point the column head temperature rose sharply to about 96.5° C. as the remaining water was azeotroped out of the base pot. Initially, the distillate receiver formed two liquid phases, but by the end of the collection of the second fraction the distillate reverted to one liquid phase. A total of 34.5 grams was collected as the second fraction. The second fraction contained about 5.7% water. A third fraction, 90.54 grams, was collected while the head temperature remained at 96.5 to 96.7° C. This product fraction [distillate (ii)] was found to be comprised of 99.95% cyclobutanone and 0.05% water by gas chromatography and trace amounts of cyclobutanol by GC mass spectroscopy. No other impurities were identified. The column was allowed to cool down and the residue in the still pot collected for analysis. The residue [distillation residue (iii)] weighed 37 grams and was comprised of about 96% cyclobutanone, 1% cyclobutanol, and unquantified levels of ketals, ethers, and other high boiling compounds.

EXAMPLE 9

Diethanolamine-Catalyzed Aldehyde Conversion

A 350 g sample of the organic layer from Example 4 containing about 88% cyclobutanone (CBON) and 0.56% cyclopropanecarboxaldehyde (CPCA)) was mixed with 1.75 g of diethanolamine (DEA) in a glass jacketed round bottom flask. The contents of the flask were heated to 50° C. with continuous stirring under an inert nitrogen atmosphere. After a reaction time at temperature of 7.5 hours, the material was sampled and heating was continued for an additional 15 hours. GC analysis of the material as this point indicated that 87.5% of the CPCA had been converted into high-boiling aldehyde condensation oligomers and greater than 96.9% of the initial CBON remained intact. The flask was cooled to 15–20° C. and 3.5 g of hydrogen-form Amberlyst 15 ion exchange resin was added with stirring. The material was kept at 15–20° C. for 4 hours, then filtered to remove the resin. When a milliliter of filtered liquid was held at 90° C. for 24 hours very little cyclobutanone was lost indicating that virtually all of the DEA was removed by the resin treatment

EXAMPLE 10

Diethanolamine-Catalyzed Aldehyde Conversion

A 100 g sample of the organic layer from Example 4 containing about 88% cyclobutanone (CBON) and 0.56% cyclopropanecarboxaldehyde (CPCA)) was mixed with 0.51 g of diethanolamine (DEA) in a glass jacketed round bottom flask. The flask was held at 60° C. under an inert nitrogen atmosphere for 7.5 hours. The material was sampled, then cooled to 50° C. and held for an additional 14.5 hours. A second sample was taken, and the flask was held at 50° C.

for another 24.5 hours. GC analysis of the material as this point showed that 100% of the CPCA had been converted into high-boiling aldehyde condensation oligomers. Greater than 91% of the initial CBON remained intact. The flask was cooled to 34° C. and 1.0 g of hydrogen-form Amberlyst 15 ion exchange resin was added with stirring. The material was maintained at 28° C. for 6.5 hours, then filtered to remove the resin. The flask was then heated to 60° C. and held at temperature for an additional 15 hours to check the stability of the CBON at higher temperatures. GC analysis showed no decrease in the cyclobutanone concentration during the final hold period indicating that virtually all of the DEA had been removed by the resin treatment.

EXAMPLE 11
Air-Oxidation Aldehyde Conversion

A 1-ml sample of the organic layer from Example 4 was stirred at 60° C. in a 7.4 ml (0.25 ounce) sealed vial with air present in the vapor space. The material was sampled after 16, 54.5 and 79.5 hours at 60° C. and analyzed. The amount of CPCA and CBON present in each sample was:

| Reaction | Percent of Starting Material Remaining | |
| --- | --- | --- |
| Time | CPCA | CBON |
| 0 | 100 | 100 |
| 16 | 44.6 | 99.7 |
| 54.5 | 25 | 99.5 |
| 79.5 | 12.5 | 99.5 |

This example shows that air oxidation under mild conditions is an effective method of destroying the aldehydes with little loss of cyclobutanone product. On a pure cyclobutanone basis the CPCA level was reduced from 0.37 weight percent to 0.043 weight percent, well within preferred aldehyde specifications.

EXAMPLE 12
Diisopropylamine-Catalyzed Aldehyde Conversion

Cyclobutanone (100 ml) having a GC assay of >99% cyclobutanone and 0.57% CPCA was mixed with distilled water and allowed to separate into two liquid phases. The organic layer comprised 94.05% cyclobutanone, 5.86% water, and 0.49% cyclopropylcarboxaldehyde. After decantation, approximately 1-ml of diisopropylamine was added to the organic layer. The mixture was heated to 60° C., maintained at temperature, and samples were taken and analyzed after 2, 6.7 and 28.7 hours of heating at 60° C. The amount of CPCA and CBON present in each sample was:

| Reaction | Percent of Starting Material Remaining | |
| --- | --- | --- |
| Time | CPCA | CBON |
| 0 | 100 | 100 |
| 2 | 73.7 | 97.6 |
| 6.7 | 47.4 | 92.3 |
| 28.7 | 28.1 | 89.4 |

The use of diisopropylamine resulted in substantial destruction of the CPCA, with modest losses of cyclobutanone.

EXAMPLE 13
Diethanolamine-Catalyzed Aldehyde Conversion

An organic, product fraction prepared as described in Example 4 was mixed with a distillate organic layer prepared as described in Example 2. Approximately 37 kg of this material, containing 0.55% CPCA and >85% cyclobutanone was mixed with 185 grams of diethanolamine in a 22-liter, jacketed, glass vessel and stirred at 50° C. for 23 hours. The mixture was cooled to 20° C. and 370 grams of hydrogen-form Amberlyst 15 ion exchange resin was added. The mixture was stirred for four hours, then filtered through a 0.45 micron filter. The CPCA level in the filtrate was found by GC analysis to be less than 0.05%, with 95% of the initial cyclobutanone remaining intact.

EXAMPLE 14
Step (5) Distillation

The purified material prepared in Example 13 was distilled using the procedure and equipment described in Example 5. The product fraction weighing 34.7 kg was analyzed by GC and found to contain 99.73% cyclobutanone, 0.1% water, less than 0.05% cyclopropanecarboxaldehyde, and no detectable cyclobutanol or cyclopropanemethanol.

EXAMPLE 15
Step (5) Distillation with Extraneous Solvent

This example demonstrates the use of an inert, azeotrope-forming solvent in the final dehydration and purification of the cyclobutanone. An organic phase (271.6 grams) obtained by the procedure described in Example 7 was charged along with 831.8 grams of methyl tert-butyl ether (MTBE) to a 2-liter base pot of a batch distillation apparatus. The distillation apparatus consisted of a 2.54 cm (1-inch) inside diameter, vacuum-jacketed, glass column packed with 1-meter (40 inches) of 3.2 mm (⅛-inch) Penn State packing. The column was equipped with a liquid dividing head, reflux timer, cooling water condenser, distillate receiver flask, electrical heating mantle, nitrogen blanketing line, and dry ice cold trap. After reaching steady state boil-up at total reflux, the reflux timer was set to 20% take-off and distillate collection was commenced. An initial distillate fraction was collected at a column head temperature of 50.6° C. to 51.9° C. This material separated into two liquid phases in the receiver flask and was found by gas chromatography to have a composition of essentially the water-MTBE azeotrope, about 3% water overall. When the water content of the still dropped below the azeotropic composition, the head temperature gradually rose to about 54° C. as nearly pure MTBE was stripped overhead. The column head temperature rose rapidly to 95.8–96.8° C. as the last traces of MTBE were distilled from the pot. Once the temperature stabilized at 96.8° C., the product fraction was collected. The distillation was stopped when the pot content had been reduced to about 50 grams and the level was well below the thermocouple in the base pot. The average purity of the product fraction was 99.8% cyclobutanone, <0.03% MTBE, and <0.1% water. The pot residue was 99.7 wt % cyclobutanone.

EXAMPLE 16
Steps III and IV Distillations Using Pressure Differential

This example illustrates operation of the step III and step IV distillations using different pressures. A process simulator was used to model a continuous two-column pressure differential distillation sequence. The step III distillation was simulated as a column consisting of 30 theoretical stages, with 15 stages above the feed point, operated at 1034 torr (0.138 MPa), with a reflux ratio of 3. The step IV distillation was simulated as a column consisting of 20 theoretical stages, with seven stages above the feed point, operated at 5170 torr (0.69 MPa), with a reflux ratio of 2.5. The fresh feed to the first column was fed at a rate of 200 kg-mole per hour with a composition as specified in Table II. The distillate from the step IV distillation column was recycled to the feed of the step III distillation column, while the distillate of the step III distillation column was fed to the step IV distillation column. Water and cyclobutanol were removed from the base of the column as column underflow from the step III distillation column and the cyclobutanone product as column underflow from the step IV distillation column. Results of the simulation are given in Table II wherein the molar flows are kg-moles/hour and the step IV distillate is recycled to step III.

TABLE II

| Stream | Molar Flows | | |
| --- | --- | --- | --- |
| | Cyclobutanone | Water | Cyclobutanol |
| Fresh Feed | 6.12 | 193.64 | 0.24 |
| Step (3) Distillate | 29.29 | 30.63 | 9.5E-7 |
| Step (3) Underflow | 0.03 | 193.63 | 0.24 |
| Step (5) Distillate | 23.30 | 30.63 | 4.1E-10 |
| Step (5) Underflow | 6.09 | 6.1E-3 | 9.5E-7 |

The invention has been described in detail with particular reference to preferred embodiments thereof, but it will be understood that variations and modifications can be effected within the spirit and scope of the invention.

We claim:

1. Process for the recovery of cyclobutanone in a purity of at least 90 weight percent from a crude product mixture comprising cyclobutanone, water and a plurality of other organic compounds resulting from the oxidation of cyclobutanol in water by the steps comprising:

(1) distilling the crude product mixture to obtain (i) a distillate comprising cyclobutanone, water, and the plurality of other organic compounds comprising cyclopropanemethanol, cyclobutanol, 3-butene-1-ol, 2-butene-1-ol, cyclopropanecarboxaldehyde, ethers and mixed ethers of cyclobutanol, cyclopropanemethanol, 3-butene-1-ol, and 2-butene-1-ol, and hemi-ketals and ketals of cyclopropanemethanol, cyclobutanol, 3-butene-1-ol and 2-butene-1-ol with cyclobutanone; and (ii) a distillation residue comprising water, metal salts, and high boiling organic compounds;

(2) allowing the distillate from step (1) to separate into (i) an organic phase comprising a minor amount of the cyclobutanone contained in the distillate and a major amount of impurities less soluble in water than cyclobutanone; and (ii) an aqueous phase comprising water, a major amount of the cyclobutanone contained in the distillate, and a minor amount of more hydrophilic impurities;

(3) distilling the aqueous phase from step (2) to obtain (i) a minor amount of distillate comprising low-boiling azeotropes comprising water and organic impurities in the aqueous phase, (ii) a major amount of distillate comprising an azeotrope of water and cyclobutanone, and (iii) a distillation residue comprising water, cyclopropanecarboxylic acid, γ-butyrolactone, cyclobutanol, cyclopropanemethanol, mixed ethers of cyclobutanol, cyclopropanemethanol, 3-butene-1-ol, and 2-butene-1-ol, and ketals formed from reactions between cyclopropanemethanol, cyclobutanol, 3-butene-1-ol and 2-butene-1-ol and cyclobutanone;

(4) allowing distillate (ii) from step (3) to separate into (i) a cyclobutanone-rich organic phase comprising cyclobutanone, water, and a plurality of close-boiling aldehydes comprising cyclopropanecarboxaldehyde and cis/trans crotonaldehydes and (ii) an aqueous phase comprising cyclobutanone and water; and (5) distilling the organic phase (i) from step (4) to obtain (i) a first distillate comprising an azeotrope of water and cyclobutanone, (ii) a second distillate comprising cyclobutanone having a puritiy of at least 90%, and (iii) a distillation residue comprising cyclobutanol, cyclopropanemethanol, mixed ethers of cyclobutanol, cyclopropanemethanol, 3-butene-1-ol, and 2-butene-1-ol, and ketals formed from reactions between cyclopropanemethanol, cyclobutanol, 3-butene-1-ol and 2-butene-1-ol and cyclobutanone.

2. Process according to claim 1 wherein the crude product mixture distilled in step (1) comprises about 2 to 20 weight percent cyclobutanone, about 70 to 97 weight percent water and about 0.2 to 10 weight percent impurities; the concentration of cyclobutanone in the distillate from step (1) is about 4 to 12 weight percent; the step (3) distillation has at least 15 equilibrium stages; the step (5) distillation has at least 12 equilibrium stages; and the second distillate (ii) of step (5) comprises cyclobutanone having a purity of at least 95%.

3. Process according to claim 1 wherein the organic phase (i) from step (2) is extracted with water using a water:organic phase weight ratio of about 1:4 to 5:1 and combining the water extract with the aqueous phase (ii) of step (2).

4. Process according to claim 1 wherein the organic phase (i) of step (4) is contacted with a molecular oxygen-containing gas or a base to convert aldehydes, comprising cyclopropanecarboxaldehyde and cis/trans crotonaldehydes, to high-boiling compounds.

5. Process according to claim 4 wherein the organic phase is contacted with air at a temperature of about 20 to 80° C.

6. Process according to claim 4 wherein the organic phase is contacted with a secondary or tertiary amine at a temperature of about 20 to 80° C.

7. Process according to claim 1 wherein step (5) is carried out in the presence of a high-boiling solvent which (1) has a boiling point of at least 30° C. above the boiling point of cyclobutanone; (2) does not form a binary azeotrope with cyclobutanone; (3) does not form a binary azeotrope with alcohols comprising cyclobutanol, cyclopropanemethanol, 3-butene-1-ol, and 2-butene-1-ol that has a boiling point within about 10° C. of the boiling point of pure cyclobutanone; and (4) is non-reactive with cyclobutanone.

8. Process according to claim 7 wherein the high-boiling, inert solvent has a boiling point of about 140 to 200° C. and is selected from the group consisting of straight and branched chain alkanes and alkyl esters of alkanoic acids.

9. Process according to claim 1 wherein step (5) is carried out in the presence of an extraneous, organic, azeotrope-forming solvent which (1) forms a heterogeneous, minimum-boiling, binary azeotrope with water or a heterogeneous, ternary, minimum-boiling, azeotrope with water and cyclobutanone that is the lowest-boiling of all binary azeotropes and pure components of the ternary minimum-boiling, azeotrope; (2) is non-reactive with cyclobutanone; and (3) does not form a binary azeotrope with alcohol contaminants that has a boiling point within about 10° C. of the boiling point of pure cyclobutanone.

10. Process according to claim 9 wherein the extraneous, organic azeotrope-forming solvent is selected from the group consisting of aliphatic, cycloaliphatic, and aromatic hydrocarbons containing up to about 7 carbon atoms; aliphatic, aromatic, and cyclic ethers containing up to about 6 carbon atoms; aliphatic and cycloaliphatic, or aromatic nitrites containing up to about 5 carbon atoms; aliphatic and cycloaliphatic ketones containing up to about 6 carbon atoms; aliphatic and cycloaliphatic halogenated hydrocarbons containing up to about 6 carbon atoms and up to about 3 chlorine, 6 fluorine, or 3 bromine atoms; and aliphatic and cycloaliphatic carboxylic acid esters containing up to about 5 carbon atoms.

11. Process according to claim 9 wherein the extraneous, organic azeotrope-forming solvent is selected from the group consisting of methyl tert-butyl ether, tert-amyl-ether, ethyl acetate, isopropyl acetate, n-pentane, n-hexane, cyclohexane, methyl isopropyl ketone, 1-chlorobutane, and 2-chlorobutane.

12. Process for the recovery of cyclobutanone in a purity of at least 90 weight percent from a crude product mixture comprising cyclobutanone, water and a plurality of other organic compounds resulting from the oxidation of cyclobutanol in water by the steps comprising:

I. distilling the crude product mixture to obtain (i) a distillate comprising cyclobutanone, water, and the plurality of other organic compounds comprising cyclopropanemethanol, cyclobutanol, 3-butene-1-ol, 2-butene-1-ol, cyclopropanecarboxaldehyde, ethers and mixed ethers of cyclobutanol, cyclopropanemethanol, 3-butene-1-ol, and 2-butene-1-ol, and hemi-ketals and ketals of cyclopropanemethanol, cyclobutanol, 3-butene-1-ol and 2-butene-1-ol with cyclobutanone; and (ii) a distillation residue comprising water, metal salts, and high boiling organic components comprising γ-butyrolactone, cyclopropanecarboxylic acid, and hemi-ketals and ketals of cyclopropanemethanol, cyclobutanol, 3-butene-1-ol and 2-butene-1-ol with cyclobutanone;

II. allowing the distillate to separate into (i) an organic phase comprising a minor amount of the cyclobutanone contained in the distillate, a major amount of impurities less soluble in water than cyclobutanone and comprising ethers, ketals, and color bodies; and (ii) an aqueous phase comprising water, a major amount of the cyclobutanone contained in the distillate, a minor amount of more hydrophilic impurities comprising alcohols and cyclopropane carboxaldehyde;

III. distilling the aqueous phase from step II at a pressure in the range of 100 to 2000 torr to obtain (i) a distillate comprising an azeotrope of water and cyclobutanone and (ii) a column underflow product comprising water, cyclopropanecarboxylic acid, γ-butyrolactone, cyclobutanol, cyclopropanemethanol, mixed ethers of cyclobutanol, cyclopropanemethanol, 3-butene-1-ol, and 2-butene-1-ol, and ketals formed from reactions between cyclopropanemethanol, cyclobutanol, 3-butene-1-ol and 2-butene-1-ol with cyclobutanone; and IV. distilling distillate (i) from step III at a pressure of about 2000 to 6000 torr to obtain (i) a distillate comprising an azeotrope of water and cyclobutanone which is recycled to the feeds of the step III distillation and (ii) a column underflow product comprising cyclobutanone having a purity of at least 90%;

provided the step IV distillation is operated at a pressure at least 760 torr greater than the pressure at which step III is operated.

13. Process according to claim 12 wherein step III is operated at a pressure of 700 to 1250 torr step IV is operated at a pressure of 3500 to 5500 torr, provided that the operating pressure of step IV is at least 2280 torr greater than the operating pressure of step III.

* * * * *